US006380161B1

(12) United States Patent
Williams et al.

(10) Patent No.: US 6,380,161 B1
(45) Date of Patent: Apr. 30, 2002

(54) COMPOSITIONS FOR TREATING CHEMOTHERAPY-RESISTANT TUMOR CELLS AND TARGETED CHEMOTHERAPY COMPOSITIONS

(75) Inventors: Taffy Williams, Lansdale, PA (US); George Tuszynski, Pittsgrove, NJ (US); Paul Actor, Phoenixville, PA (US)

(73) Assignees: Inkine Pharmaceutical Company, Inc., Blue Bell; Philadelphia Health and Education Corporation, Philadelphia, both of PA (US)

( * ) Notice: Subject to any disclaimer, the term of this patent is extended or adjusted under 35 U.S.C. 154(b) by 0 days.

(21) Appl. No.: 09/597,766

(22) Filed: Jun. 20, 2000

Related U.S. Application Data
(60) Provisional application No. 60/140,309, filed on Jun. 21, 1999.

(51) Int. Cl.$^7$ .............................................. A91K 38/00
(52) U.S. Cl. ............................ 514/12; 514/17; 514/16; 514/15; 514/2; 530/327; 530/329; 530/330; 435/6
(58) Field of Search ................................. 530/329, 327, 530/330; 514/12, 17, 16, 15, 2; 435/6

(56) References Cited

U.S. PATENT DOCUMENTS

| | | | |
|---|---|---|---|
| 5,155,038 A | 10/1992 | Eyal et al. ...................... | 514/8 |
| 5,187,266 A | 2/1993 | Farquhar et al. .............. | 536/6.4 |
| 5,190,918 A | 3/1993 | Deutch et al. ................. | 514/15 |
| 5,190,920 A | 3/1993 | Eyal et al. ...................... | 514/17 |
| 5,200,397 A | 4/1993 | Deutch et al. ................. | 514/15 |
| 5,357,041 A | 10/1994 | Roberts et al. ............... | 530/326 |
| 5,367,059 A | 11/1994 | Tuszynski et al. ........... | 530/395 |
| 5,426,100 A | 6/1995 | Deutch et al. ................. | 514/15 |
| 5,506,208 A | 4/1996 | Eyal et al. ...................... | 514/17 |
| 5,510,239 A | * 4/1996 | Baracchini et al. ............ | 435/6 |
| 5,591,715 A | 1/1997 | Coon et al. .................... | 514/10 |
| 5,625,043 A | 4/1997 | Priebe et al. .................. | 536/44 |
| 5,648,461 A | 7/1997 | Eval et al. ..................... | 530/329 |
| 5,654,277 A | 8/1997 | Eyal et al. ..................... | 514/18 |
| 5,681,812 A | 10/1997 | Coon et al. .................... | 514/10 |
| 5,770,563 A | * 6/1998 | Roberts et al. ................. | 435/6 |
| 5,776,891 A | 7/1998 | Coon et al. .................... | 514/10 |
| 5,801,154 A | 9/1998 | Baracchini et al. ........... | 514/44 |
| 5,807,838 A | 9/1998 | Baracchini, Jr. et al. ...... | 514/44 |
| 5,840,692 A | 11/1998 | Deutch et al. ................. | 514/12 |
| 5,843,903 A | 12/1998 | Schally et al. ................ | 514/16 |
| 5,874,412 A | 2/1999 | Priebe et al. .................. | 514/34 |

FOREIGN PATENT DOCUMENTS

| | | | | |
|---|---|---|---|---|
| EP | 0 443 404 A1 | 8/1991 | ............ | C07K/7/00 |
| EP | 478101 A2 | * 1/1992 | | |
| EP | 0 578 342 A2 | 1/1994 | ........... | C07K/15/14 |
| WO | WO 92/17499 | 10/1992 | ........... | C07K/15/00 |
| WO | WO 98/35688 | 8/1998 | .......... | A61K/38/00 |
| WO | WO 01/05968 A1 | 1/2001 | ........... | C12N/15/12 |

OTHER PUBLICATIONS

Arap et al., "Cancer Treatment by Targeted Drug Delivery to Tumor Vasculature in a Mouse Model", Science, vol. 279, pp. 377–380, Jan. 16, 1998.*

Anderson, "The Use of Esters of N–Hydroxysuccinimide in Peptide Synthesis," J. Am. Chem. Soc. 86:1839 (1964).

Arap, "Cancer Treatment by Targeted Drug Delivery to Tumor Vasculature in Mouse mOdel," Science 279:377–80 (1998).

Bleicher et al., "Biochemical Mechanism of Cross–resistance to Paclitaxel in a Mitomycin c–Resistant Human Bladder Cancer Cell Line," Cancer Lett 150(2):129–35 (2000).

Choudhuri et al. "Reversal of Resistance Against Doxorubicin by a Newly Developed Compound, Oxalyl Bis(N–phenyl)hydroxamic Acid in Vitro," Anti–Cancer Drugs 9:825–32 (1998).

Dun et al., "Discovery of Differentially Expressed Genes Associated with Paclitaxel Resistance Using cDNA Array Technology: Analysis of Interleukin (IL) 6, IL–8, and Monocyte Chemotactic Protein 1 in the Paclitaxel–resistant Phenotype," Clin. Cancer Res. 5(11):3445–53 (1993).

Elias, Anthony D., "Advances in the diagnosis and management of sarcomas," Current Opinion in Oncology 4:681–8 (1992).

Gonzalez–Garay, "A β–Tubulin Leucine Cluster Involved in Microtubule Assembly and Paclitaxel Resistance," J. Biol. Chem., 274:23875–882 (1999).

Harris et al., "Mechanisms of Multidrug Resistance in Cancer Treatment," Acta Oncological 31:205–13 (1992).

Janaky et al., "Analogues of luteinizing hormone–releasing hormone containing cytotoxic groups," Proc Batl. Acad. Sci. USA 89:972–76 (1992).

Janaky et al., "Short–Chain analogs of luteinizing hormone–releasing hormone containing cytotoxic moieties," Proc. Natl. Acad. Sci. USA 89:10203–7 (1992).

Magri et al., "Modified Taxols, 4. Synthesis and Biological Activity of Taxols Modified in the Side Chain," Journal of Natural Products 51(2):298–306 (1988).

Monzo et al., "Paclitaxel resistance in non–small–cell lung cancer associated with beta–tubulin gene mutations," J. Clin. Oncol. 17(6):1786–93 (1999).

Nagy et al., "Cytotoxic Analogs of Luteinizing Hormone–Releasing Hormone Containing Doxorubicin," PNAS 93:7269–73 (1996).

(List continued on next page.)

Primary Examiner—Karen Cochrane Carlson
Assistant Examiner—Stephen Tu
(74) Attorney, Agent, or Firm—Finnegan, Henderson, Farabow, Garrett & Dunner, L.L.P.

(57) ABSTRACT

The present invention provides methods and compositions for treating cancer and chemotherapy-resistant cancers comprising a chemotherapeutic agent conjugated to or coadministered with a peptide.

15 Claims, 9 Drawing Sheets

OTHER PUBLICATIONS

O'Brien et al., "Glutathione peptidomimietic drug modulator of multidrug resistance–associated protein," J Pharmacol Exp Ther 291(3):1348–55 (1999).

Priebe et al., "Removal of the basic center from doxorubicin partially overcomes multidrug resistance and decreases cardiotoxicity," Anti–Cancer Drugs 4:37–48 (1993).

Rahman, "Modulation of Multidrug Resistance in Cancer Cells by Liposome Encapsulated Doxorubicin," J. Liposome Res. 4:575–604 (1994).

Reinecke et al., "Growth Inhibitory Effects of Paclitaxel on Human Epitheloid Sarcoma in Vitro: Heterogeneity of Response and the Multidrug Resistance Phenotype," Cancer 88(7):1614–22 (2000).

Sackett, Fojo T., "Taxanes and other microtubule stabilizing agents," Cancer Chemother Biol Response Modif 18:59–80 (1999).

Safavy, "Paclitaxel Derivatives for Targeted Therapy of Cancer: Toward the Development of Smart Taxanes," J. Med. Chem. 42:4919–24 (1999).

Schuurhuis et al., "Changes in subcellular doxorubicin distribution and cellular accumulation alone can largely account for doxorubicin resistance in SW–1573 lung cancer and MCF–7 breast cancer multidrug resistant tumor cells," BJC 898–908 (1993).

Stan et al., "Antineoplastic Efficacy of Doxorubicin Enzymatically Assembled on Galactose Residues of a Monoclonal Antibody Specific for the Carcinoembryonic Antigen," Cancer Res. 59:115–21 (1999).

Tuszynski et al., "Localization of Thrombospondin and Its Cysteine–Serine–Valine–Threonine–Cysteine–Glycine–Specific Receptor in Human Breast Carcinoma," Laboratory Investigation 70(2):228–32 (1994).

Yang et al., "Reversal of Doxorubin Resistance by Doxorubicin–gallium–transferrin Conjugate in Human Breat Cancer Cell Lines," Proc. Am. Assn. Cancer Res. 40:4377 (1999).

Zunino et al., "Interaction of Daunomycin and its Derivatives with DNA," Biochim. Biophys. Acta 227:489–98 (1972).

Asakura, et al., "Drug Conjugate of Doxorubicin with Glutathione is a Potent Reverser of Multidrug Resistance in Rat Hepatoma Cells," Anti–Cancer Drugs, 8(2): 199–203 (1997).

Asakura, et al., "Glutathione–Doxorubicin Conjugate Expresses Potent Cytotoxicity by Suppression of Glutathione S–Transferase Activity: Comparison Between Doxorubicin–Sensitive and –Resistant Rat Hepatoma Cells," British Journal of Cancer, 76(10): 1333–1337 (1997).

Barinaga, "Peptide Guided Cancer Drugs Show Promise in Mice," Science, 279:323–324 (1998).

Mazzoni, et al., "Comparative Distribution of Free Doxorubicin and Poly–L–Aspartic Acid Linked Doxorubicin in MS–2 Sarcoma Bearing Mice," Cancer Drug Delivery, 3(3): 163–172 (1986).

Nagy, et al., "Cytotoxic Analogs of Luteinizing Hormone Releasing Hormone Containing Doxorubicin or 2–Pyrrolinodoxorubicin, a Derivative 500–1000 Times More Potent," Proc. Natl. Acad. Sc., 93(14): 7269–7273 (1996).

Pratesi, et al., "Poly–L–Aspartic Acid as a Carrier for Doxorubicin: A Comparative In Vivo Study of Free and Polymer–Bound Drug," British Journal of Cancer, 52: 841–848 (1985).

Safavy, et al., "Paclitaxel Derivatives for Targeted Therapy of Cancer Toward the Development of Smart Taxanes," J. Med. Chem., 42(23): 4919–4924 (1999).

Zunino, et al., "Comparison of Antitumor Effects of Daunorubicin Covalently Linked to Poly–L–Amino Acid Carriers," Eur J. Cancer Clin Oncol, 20(3): 421–425 (1984).

* cited by examiner

FIG. 9

1 mM DOX IN ALL TREATMENTS

- BUFFER
- 10mM CYS(ACM)-SER-VAL-THR-CYS(ACM)-GLY
- 10mM ALA-SER-VAL-THR-ALA-ARG
- 5 mM ALA-SER-VAL-THR-ALA-ARG
- 1 mM ALA-SER-VAL-THR-ALA-ARG
- 0.1 mM ALA-SER-VAL-THR-ALA-ARG

%VIABILITY

```
                         SEQUENCE LISTING

<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Ser Val Thr Cys Gly
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ser Val Thr Ala Arg
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Cys Thr Gly Ser Cys
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Ser Val Thr Cys Arg
 1               5

<210> SEQ ID NO 5
<211> LENGTH: 5
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 5

Ser Val Thr Cys Gly
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Cys(Acm)
<221> NAME/KEY: MOD_RES
<222> LOCATION: (5)
<223> OTHER INFORMATION: Cys(Acm)

<400> SEQUENCE: 6

Cys Ser Val Thr Cys Gly
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Thr Cys Gly
```

COMPOSITIONS FOR TREATING CHEMOTHERAPY-RESISTANT TUMOR CELLS AND TARGETED CHEMOTHERAPY COMPOSITIONS

PRIORITY INFORMATION

This application claims priority to U.S. Provisional application Ser. No. 60/140,309, filed Jun. 21, 1999.

TECHNICAL FIELD

Compositions and methods for treating doxorubicin, paclitaxel, or multidrug-resistant tumor cells are provided. The compositions include a doxorubicin-peptide conjugate as well as peptide coadministered with doxorubicin. The compositions of this invention also include a paclitaxel-peptide conjugate as well as peptide coadministered with paclitaxel. The conjugate compositions, as well as the coadministration therapy, will be useful in treating both patients with doxorubicin, paclitaxel, or multidrug-resistant cancer and those with normal cancer. The compositions of the invention are also more effective, and require smaller doses, than the chemotherapy agent alone because the peptide serves to target the chemotherapy agent to the tumor cells.

BACKGROUND OF THE INVENTION

Doxorubicin is the most commonly used anticancer chemotherapeutic agent, and it has the widest spectrum of antitumor effects. Nagy et al., *Cytotoxic analogs of luteinizing hormone-releasing hormone containing doxorubicin*, PNAS 93:7269–7273 (1996). It is an anthracycline derived from *Streptomyces peucetius* var. *coesius*. Stan et al., *Antineoplastic Efficacy of Doxorubicin Enzymatically Assembled on Galactose Residues of a Monoclonal Antibody Specific for the Carinoembryonic Antigen, Cancer Res.* 59:115–121 (1998). It is has two regions, named adriamycinone and daunosamine. The structure of doxorubicin is shown in FIG. 1. Doxorubicin ("Dox") intercalates itself into double-stranded nucleic acids, inhibiting DNA and RNA synthesis, and affects the stability of DNA-topoisomerase II complexes. In order to be effective, Dox must accumulate in the cell and reach certain threshold levels.

Paclitaxel is a common chemotherapeutic agent often used to treat breast cancer. It is distributed by Bristol-Myers Squibb under the tradename TAXOL™. It is a natural product with antitumor activity. It is obtained via a semi-synthetic process from *Taxus baccata* (the Pacific Yew Tree). The chemical name for paclitaxel is 5β,20-Epoxy-1,2α,4,7β,13α-hexahydroxytax-11-en-9-one 4,10-diacetate 2-benzoate 13-ester with (2R,3S)-N-benzyol-3-phenylisoserine. The structure of paclitaxel is shown in FIG. 2.

Paclitaxel acts as an antimicrotubule agent by promoting the assembly of microtubules from tubulin dimers and stabilizing microtubules by preventing depolymerization. This stability results in the inhibition of the normal dynamic reorganization of the microtubule network that is essential for vital interphase and mitotic cellular functions. In addition, paclitaxel induces abnormal arrays or "bundles" of microtubules throughout the cell cycle and multiple arrays of microtubules during mitosis.

The most significant problem oncologists face in the treatment of cancer, is the existence of drug resistance in tumors resulting in decreased cytotoxicity of chemotherapy agents. Some cancers are drug resistant prior to treatment, whereas others develop drug resistance during treatment.

In many instances, when a tumor develops drug resistance in response to treatment with one agent, such as Dox or paclitaxel, cross-resistance develops to structurally and functionally unrelated drugs such as vinblastine and cisplatin. Choudhuri et al., *Reversal of resistance against doxorubicin by a newly developed compound, oxalyl bis(N-phenyl)hydroxamic acid in vitro, Anti-Cancer Drugs* 9:825–832 (1998). This pattern of resistance is named multidrug resistance (MDR). Researchers have identified a gene MDR1, and its gene product, p-glycoprotein, in MDR tumors. P-glycoprotein functions as an efflux pump, preventing accumulation of drugs and hence reducing cytotoxicity. This mechanism is responsible for one type of doxorubicin resistance in cancer cells. Rahman, *Modulation of Multidrug Resistance in Cancer Cells by Liposome Encapsulated Doxorubicin, J. Liposome Res.* 4:575–604 (1994).

Paclitaxel is a substrate for the multidrug resistant pump, which is also termed gP170, and cells selected for high levels of resistance to this drug have increased levels of gP170. Gonzalez-Garay, *A β-Tubulin Leucine Cluster Involved in Microtubule Assembly and Paclitaxel Resistance, J. Biol. Chem.* 274:23875–23882 (1999). Other paclitaxel resistance mechanisms have also been proposed including changes in the expression of specific β-tubulin genes and mutations in β-tubulin. Id.

Other mechanisms for chemotherapy resistance include: glutathione tranferances and detoxification mechanisms; topoisogenetic recombination, DNA transcription, chromosome segregation; and DNA repair. Harris et al., *Mechanisms of Multidrug Resistance in Cancer Treatment, Acta Oncological* 31:205–213 (1992).

Researchers have experimented with numerous different strategies for overcoming doxorubicin resistance. One such strategy involves the use of nonionic amphipathic diesters of fatty acids or a reverse poloxmer to treat MDR cancer. U.S. Pat. No. 5,681,812. Oligonucleotides specifically hybridizable with nucleic acids encoding MDR associated proteins have also been developed. U.S. Pat. No. 5,807,838. An hydroxamic acid derivative, oxalyl bis(N-phenyl) hydroxamic acid, has also shown promising results in reversing MDR. Choudhuri et al., *Reversal of Resistance Against Doxorubicin by a Newly Developed Compound, Oxalyl Bis(N-phenyl)hydroxamic Acid in Vitro, Anti-Cancer Drugs,* 9:825–832 (1998). Another strategy proposes the use of liposome encapulated doxorubicin to overcome doxorubicin resistance. Rahman, *Modulation of Multidrug Resistance in Cancer Cells by Liposome Encapsulated Doxorubicin, J. Liposome Res.* 4:575–604 (1994).

Doxorubicin conjugates have also been developed. Doxorubicin conjugated to a gallium-transferrin compound has been shown to reverse drug resistance in breast cancer cell lines. Yang et al., *Reversal of doxorubicin resistance by doxorubicin-gallium-transferrin conjugate in human breast cancer cell lines, Proc. Am. Assn. Cancer Res.* 40:4377 (1999). Analogs to luteinizing hormone-releasing hormone ("LH-RH") have also been conjugated to doxorubicin, resulting in a more potent, targeted anticancer agent for tumors that possess receptors for LH-RH. Nagy et al., *Cytotoxic Analogs of Luteinizing Hormone-Releasing Hormone Containing Doxorubicin or 2-Pyrrolinodoxorubicin, a Derivative 500–1000 Times More Potent,* PNAS 93:7269–7273 (1996). Monoclonal antibodies have also been conjugated to doxorubicin, resulting in more potent treatment compositions. Stan et al., *Antineoplastic Efficacy of Doxorubicin Enzymatically Assembled on Galactose Residues of a Monoclonal Antibody Specific for the Carcinoembryonic Antigen, Cancer Res.* 59:115–121 (1999).

While doxorubicin conjugates have been considered previously, the art has taught away from derivatization of the amino group of the doxorubicin on the adriamycinone moiety. Neutralization of the dausonamine nitrogen of doxorubicin has previously resulted in severe loss of cytotoxic activity. See Nagy, *Cytotoxic Analogs of Luteinizing Hormone-Releasing Hormone containing doxorubicin or 2-pyrrolinodoxorubicin, a derivative 500–1000 times more potent*, PNAS 93:7269–7273 (1996); Zunino et al., *Interaction of Daunomycin and its Derivatives with DNA*, Biochim. Biophys. Acta 227:489–498 (1972). Such a modification was thought to inactivate the doxorubicin. Instead, those in the art have followed a strategy more difficult to accomplish involving modification of the $CH_2OH$ group in the adriamycinone portion of doxorubicin.

A previous paclitaxel-peptide conjugate has been constructed with a bombesin/gastrin-releasing peptide receptor-recognizing peptide: Gln-Trp-Ala-Val-Gly-His-Leu (SEQ ID NO: 8). Safavy, *Paclitaxel Derivatives for Targeted Therapy of Cancer: Toward the Development of Smart Taxanes*, J. Med. Chem. 42:4919–4924 (1999).

SUMMARY OF THE INVENTION

It is an object of the present invention to provide a method for treating a patient suffering from cancer, wherein a cancer chemotherapy agent is selected, conjugated to a peptide, and administered to the patient.

It is a further object of the invention to provide a method of treating a patient suffering from cancer, wherein a cancer chemotherapy agent is selected, a peptide is selected, and the agent and peptide are coadministered to the patient.

It is a further object of the invention to provide a composition for treating a patient suffering from cancer, wherein the composition comprises a chemotherapy agent and a peptide.

BRIEF DESCRIPTION OF THE DRAWINGS

FIG. 9 (Effect of Ala-Ser-Val-Thr-Ala-Arg on Doxorubicin Toxicity of Doxorubicin Resistant CHO Cells) shows the effect of coadministering the peptide Ala-Ser-Val-Thr-Ala-Arg (SEQ ID NO: 2) with doxorubicin against doxorubicin and multidrug-resistant cells.

DETAILED DESCRIPTION OF THE INVENTION

Figure 1:
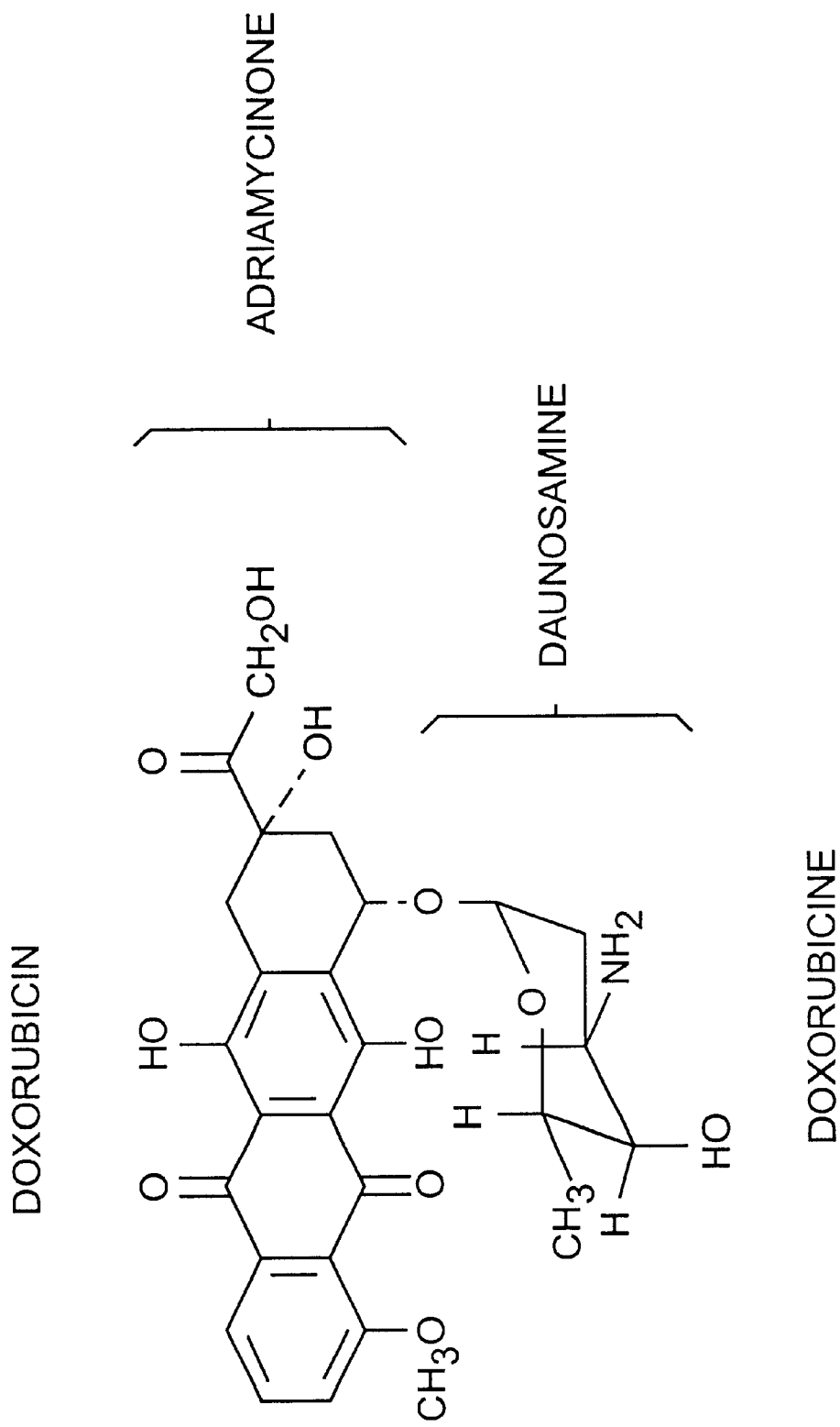
FIG. 1 (Doxorubicin) is a drawing of doxorubicin.
Figure 2:
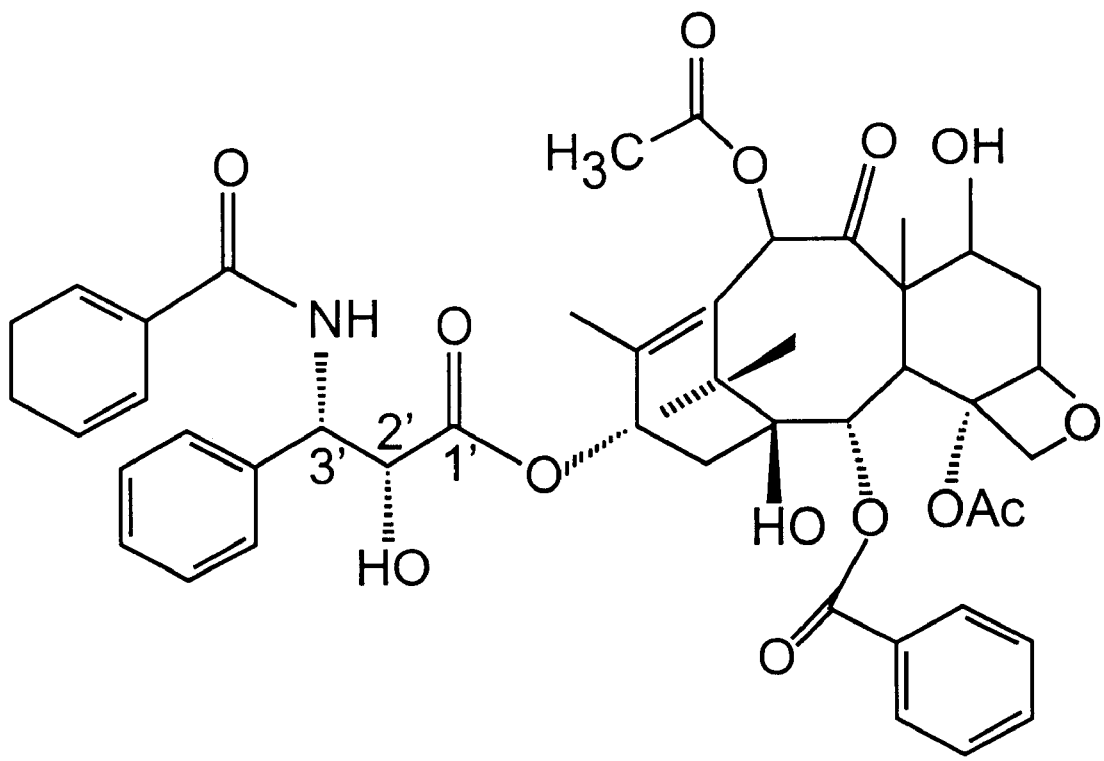
FIG. 2 (Paclitaxel) is a drawing of paclitaxel.
Figure 3:
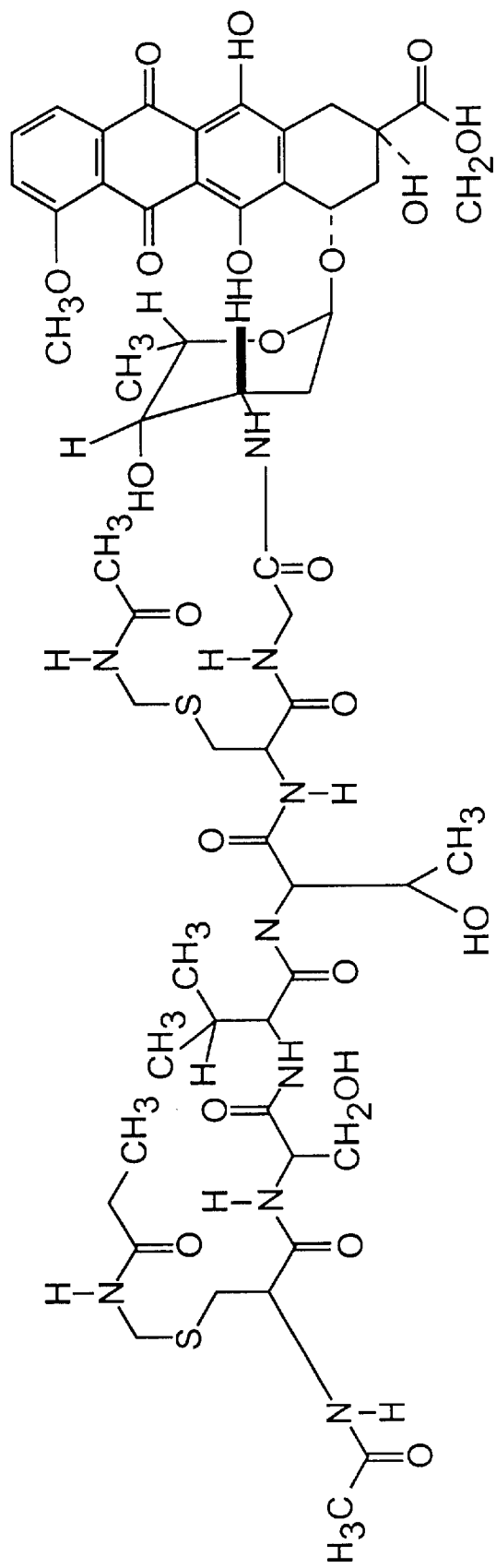
FIG. 3 (Doxorubicin-Peptide Conjugate) is a drawing of a doxorubicin-peptide conjugate ("Dox-P") of the present invention, where the doxorubicin is linked through its amino terminus to the carboxy terminus of the peptide Cys(Acm)-Ser-Val-Thr-Cys(Acm)-Gly (SEQ ID NO: 6). The linkage is an amide linkage. The peptide's amino terminus is modified with an Acm group for protection during the linkage with the doxorubicin, and the Acm group is left on the conjugate.

The present invention relates to chemotherapeutic agents conjugated to or coadministered with peptides. Chemotherapeutic agent-peptide conjugates can be produced by linking the chemotherapeutic agent to peptides using various methods of chemical synthesis. Chemotherapeutic agents can also be coadministered with peptides of the present invention. These two strategies can be used independently or they can be combined by coadministering a chemotherapeutic agent-peptide conjugate with an additional peptide of the present invention.

Various chemotherapeutic agents can be used in the present invention. Those agents that tend to lose effectiveness due to resistant tumor cells are preferable. Additionally, preferred compounds include those that would benefit from targeted administration due to toxicity, for example. Acceptable agents including the following:

alkylating agents (bisulfan, carboplatin, cisplatin, thiotepa);

nitrogen mustards (melphalan, cyclophospamide, chlorambucil, ifosfamide, mechlorethamine);

nitrosoureas (carmustine, streptozocin);

antibiotics (doxorubicin, bleomycin, danuorubicin, actinomycin D, idarubicin, fludarabine, floxuradine, 5-flurouracil, antracylcine, plicamycin, mitomycin C, mitoxantrone, cytarabine, cladribine);

vinca alkyloids (vincristine, vinblastine);

hormonal agonists and antagonists (androgens including: nilutamide and testolactone; antiandrogens including: bicalutamide and flutamide; antiestrogens including: anastrozole, toremitine, letrozole, and tamoxifen; estrogens including: estradiol; gonadotropin releasing hormone analogs including: leuprolide acetate and goserelin acetate; and progestins including: medroxyprogesterone and megestrol); and other agents (including paclitaxel, camphothecan, topotecan, vincristine, vinblastine, colchicine, methotrexate, mercaptopurine, irinotecan, B-methasone, dicarbazine, aspartgenace, etoposide, germcitabine, altretamine, hydroxyurea, mitotane, vinurelbine, L-asparginase, paclitaxel, docetaxal, tretinoin, temiposide, ricin, cytoxin, saintopin, ellipticin, azatoxin, SQZ, dinalin, and VP16).

This invention is most useful when the chemotherapy agent is highly toxic, as the peptide conjugation and/or coadministration strategy can both reduce the toxicity of the agent and allow less composition to be administered due to increased efficacy. Thus the invention is useful for treating resistant cancers, but it is particularly beneficial to use them to treat nonresistant cancers. Moreover, by targeting the chemotherapy agents to the tumor cells this invention allows for more effective treatment at lower doses. One preferred composition of the present invention contains doxorubicin. Another preferred composition contains paclitaxel.

Peptides of the present invention include peptide sequences from thrombospondin that bind to the thrombospondin receptor. These peptides can be selected from the amino acids at or near the receptor binding sequence of thrombospondin, Cys-Ser-Val-Thr-Cys-Gly (SEQ ID NO: 1), or from other known peptides with thrombospondin activity. See, U.S. patent appln. Ser. Nos.: 08/476,134 and 09/197,770; and U.S. Pat. Nos.: 5,190,918; 5,155,038; 5,190,920; 5,200,397; 5,367,059; 5,506,208; 5,648,461; 5,426,100; 5,654,277; 5,840,692; 5,357,041; and 5,770,563. Specifically, these include peptides binding to the TSP-1 receptor with an affinity from about $10^{-6}$ M to about $10^{-10}$ M, preferably from about $10^{-7}$ M to about $10^{-9}$ M, most preferably about $10^{-8}$ M.

Peptides can also be identified by their capacity to bind to the thrombospondin receptor. Such peptides can be developed and identified by using a phage display peptide library kit, such as that available from New England Biolabs (Beverly, Mass.). Phage display describes a selection technique in which a peptide or protein is expressed as a fusion with a coat protein of a bacteriophage, resulting in display of the fused protein on the exterior surface of the phage virion, while the DNA encoding the fusion resides within the virion. Phage display can be used to create a physical linkage between a vast library of random peptide sequences to the DNA encoding each sequence, allowing rapid identification of peptide ligands for a variety of target molecules (including receptors) by an in vitro selection process called biopanning. This technique is carried out by incubating a library of phage-displayed peptides with a plate (or bead) coated with the target receptor, washing away the unbound phage, and eluting the specifically-bound phage. The eluted phage is then amplified and taken through additional cycles of biopanning and amplification to successively enrich the pool of phage in favor of the tightest binding sequences. After 3–4 rounds, individual clones are characterized by DNA sequencing and ELISA. Appropriate peptides can be made based on the oligonucleotide sequence identified.

Additionally, random peptides can be screened for their ability to bind to the thrombospondin receptor or for their ability to promote the activity of doxorubicin paclitaxel, or other chemotherapeutic agents when conjugated to or coadministered with them. They can be screened by the Affinity Sensor System or the Adhesion Studies as discussed in the Examples below. Other methods of screening for peptides that bind to the receptor would be readily known to one of skill in the art.

The peptides can be from 3 to 100 amino acids in length, preferably 3 to 50, 3 to 20, or 4 to 11 amino acids in length, most preferably 4, 5, 6, 7, 9, or 11 amino acids in length. The longer peptides may be useful as they could include the heparin binding domains of the thrombospondin protein, which flank the Cys-Ser-Val-Thr-Cys-Gly (SEQ ID NO: 1) region. Preferred peptides include Cys-Ser-Val-Thr-Cys-Gly (SEQ ID NO: 1), Cys(Acm)-Ser-Val-Thr-Cys(Acm)-Gly (SEQ ID NO: 6), Ala-Ser-Val-Thr-Ala-Arg (SEQ ID NO: 2), Cys-Ser-Val-Thr-Cys-Arg (SEQ ID NO: 4), and Ser-Val-Thr-Cys-Gly (SEQ ID NO: 5), and Val-Thr-Cys-Gly (SEQ ID NO: 7). Most preferable peptides include Cys-Ser-Val-Thr-Cys-Gly (SEQ ID NO: 1), Cys(Acm)-Ser-Val-Thr-Cys(Acm)-Gly (SEQ ID NO: 6), and Ala-Ser-Val-Thr-Ala-Arg (SEQ ID NO: 2).

The Cys-Ser-Val-Thr-Cys-Gly (SEQ ID NO: 1) and the Cys(Acm)-Ser-Val-Thr-Cys(Acm)-Gly (SEQ ID NO: 6) are expected to behave similarly in the present invention. The first peptide is subject to oxidation at the sulfur atoms on the two cystine residues, and can become cyclized or linked to other molecules of the peptide in a polymer fashion. The modified peptide remains in the linear conformation. Other blocking strategies can be used to prevent the peptide from oxidizing and forming disulfide bonds, as the oxidized peptide may be less stable. These blocking strategies include alkylation with a methyl or other alkyl group and acetylation.

Peptides of the present invention include those with unnatural or non-amino acids. These peptides, which would be made by chemical synthesis, include those with modified amino acids or other moieties in place of an amino acid. Such other moieties could include fluorine, chlorine, organic compounds such as alcohols, organic ring structures, and hydroxyacids. Amino acids or peptides in the d-orientation can also be used, as can peptides in the reverse orientation. One could also mimic the peptide with organic molecules having a similar structure and conformation. The inclusion of unnatural or non-amino acids could be made to stabilize the peptide, block metabolization (in the case of a fluorine), or to create a conformational change in the peptide which would increase its binding affinity to the TSP-1 receptor.

One of the compositions of the present invention was produced by linking the doxorubicin through its amino terminus to the carboxy terminus of the peptide Cys(Acm)-Ser-Val-Thr-Cys(Acm)-Gly (SEQ ID NO: 6) through an amide linkage. The peptide's amino terminus was modified with an acetyl group for protection during the linkage with the doxorubicin, and the acetyl group was left on the conjugate.

Another composition of the invention was produced by linking the paclitaxel to the carboxy terminus of the peptide Cys(Acm)-Ser-Val-Thr-Cys(Acm)-Gly (SEQ ID NO: 6) through a succinyl linker.

Other methods of conjugation would be readily apparent to one skilled in the art. First, conjugation could occur though the primary hydroxyl of the adriamycinone through an ester linkage with the carboxylic acid end of the amino carboxylic acid. The amino group at the other terminus of the amino acid linker can then be used to form an amide with the carboxylic acid of the terminal glycine in the peptide.

Second, the amino group of the terminal cysteine of the thrombospondin can be used to form an amide with one end of a dicarboxylic acid while the other end of the dicarboxylic acid can be used with the amino group of the daunosamine fragment of the doxorubicin, thus forming a bisamide. Alternatively, the same dicarboxylic acid might be used with the amino group of the cysteine and the primary hydroxyl of the adriamycinone aglycone of doxorubicin, thus forming an amidoester.

Another composition of the present invention was produced by linking the paclitaxel through a succinyl linker to the amino terminus of the peptide Cys(Acm)-Ser-Val-Thr-Cys(Acm)-Gly (SEQ ID NO: 6) through an ester-amide linkage. The ester linkage is between the paclitaxel and the succinyl linker, and the amide linkage is between the succinyl linker and the amino terminus of the peptide.

The compositions of the present invention may be formulated in a pharmaceutical composition, which may include carriers, thickeners, diluents, buffers, preservatives, surface active agents, liposomes, or lipid formulations, and the like. The pharmaceutical compositions may also include one or more additional active ingredients such as other chemotherapy agents, antimicrobial agents, antiinflammatory agents, anesthetics, and the like.

The pharmaceutical composition may be administered in a number of ways depending on whether local or systemic treatment is desired, and on the area to be treated. Administration may be topically (including on the skin, ophthalmically, vaginally, rectally, intranasally), orally, by inhalation, or parenterally, for example by intravenous drip, subcutaneous, intratumor, intraperitoneal, or intramuscular injection.

With formulations for topical administration may include ointments, lotions, creams, gels, drops, suppositories, sprays, liquids and powders. Conventional pharmaceutical carriers, aqueous, powder or oily bases, thickeners, and the like may be necessary or desirable. Compositions for oral administration include powders or granules, suspensions or solutions in water or nonaqueous media, capsules, or tablets. Thickeners, flavorings, diluents, emulsifiers, dispersing aids or binders may be desirable. Formulations for parenteral administration may include sterile aqueous solutions optionally containing buffers, liposomes, diluents and other suitable additives.

Dosing is dependent on the severity and responsiveness of the condition to be treated, with course of treatment lasting from several days to several months or until a cure is effected or a diminution of disease state is achieved.

Optimal dosing schedules and dosing amounts can be calculated based on the chemotherapy agent alone. The conjugated compound or the coadministered compound can then be compared to the chemotherapy agent alone, and the dosages can be adjusted accordingly. For instance, optimal dosages are generally 10×below the lethal dose. The $LD_{50}$ (the dose that kills 50% of the test animals) can be determined for the chemotherapy agent alone as well as for the composition of the present invention. These calculations should preferably be performed in two animal models. The composition's half life can also be determined in one or more animal models, and can be used to determine a dosing schedule. The differences between the $LD_{50}$ and the half life for the chemotherapy agent alone and the composition of the present invention can be used to adjust the dosages. After patients are treated, the dosages can be reduced in amount or frequency if a patient exhibits signs of toxicity or increased if the patient tolerates the dosage regime.

Optimal dosing schedules can also be calculated from measurements of drug accumulation in the body. Persons of ordinary skill in the art can easily determine optimum dosages, dosing methods, and repetition rates. Optimum dosages may vary depending on the potency of the composition, and can generally be estimated based on $LD_{50}$'s from in vitro studies. In general, Dox-P conjugate dosage is from about 5 mg/kg to about 30 mg/kg, more preferably about 10 mg/kg to about 15 mg/kg and the compositions may be administered as a constant infusion using a pump or other device, over a period of an hour or three hours to 24 hours, multiple times a day (e.g., 2 or 3 times a day), once daily, weekly, monthly, or yearly. The most commonly used dosage of doxorubicin, when used in the absence of other chemotherapy agents, is about 60 to about 75 mg/m² given every 21 days, and when used in conjunction with other chemotherapy agents, is about 40 to about 50 mg/m² given every 21 days.

In general, paclitaxel-p conjugate dosage is from about 50 mg/m² to about 250 mg/m², preferably from about 100 mg/m² to about 200 mg/m², more preferably from about 135 mg/m² to about 175 mg/m². This dosage can be administered IV over about 1 hour to about 36 hours, preferably over about 3 hours to about 24 hours, and the compositions may be administered as a constant infusion using a pump or other device, once weekly, once every two weeks, once every three weeks, monthly, or yearly. Dosages of both dox-p and paclitaxel-p can also be lower than the standard recommended dosages because the peptide-conjugate allows for increased specificity, and thus a lower dose.

EXAMPLES

The following examples are presented for illustrative purposes only and are not intended to limit the scope of the invention in any way.

Example 1

Preparation of a Doxorubicin-Peptide Conjugate

A doxorubicin-peptide conjugate ("Dox-P") was produced by linking the doxorubicin through its amino terminus to the carboxy terminus of the peptide Cys(Acm)-Ser-Val-Thr-Cys(Acm)-Gly (SEQ ID NO: 6), through an amide linkage. The peptide's amino terminus is modified with an Acm for protection during the linkage with the doxorubicin, and the Acm group is left on the conjugate. Depending on the conditions used for modification, the two OH groups on the peptide may also be modified with an Acm. According to mass determinations, however, the peptide used in these Examples had only one additional Acm group. Applicants believe that the Acm group is on the amino terminus of the peptide.

The method begins with a derivatized thrombospondin peptide, which has its sulfur groups of the cysteine residues protected by acetamidomethyl (Acm) groups. Under argon, the peptide (35 mg, 0.05 mM) was suspended in acetic anhydride (10 mL) and, with stirring, triethylamine (1 mL) was added. Stirring was continued until dissolution was complete (about 1 hour). The resulting solution was yellowish.

The flask was transferred to a room temperature water bath and the solvents removed by pumping at about $10^{-4}$ torr. Solvent removal took about 10 minutes. The residue was dissolved in water (about 5 mL) to hydrolyze any anhydride that had been formed at the carboxylic acid end of the thrombospondin peptide and the resulting aqueous solution evaporated to dryness again. The procedure with water was repeated a second time. The resulting residue was yellow-brownish.

The yellow-brown material was taken up in anhydrous ethanol and then evaporated to dryness again at high vacuum to remove traces of water which might have remained and the residue was then taken up in dry DMF (2 mL) and treated, successively, with N-hydroxysuccinimide (11.5 mg, 0.10 mM) and ethyl 3-(3-dimethylamino)-carbodiimide (19.1 mg, 0.10 mM). After stirring the reaction mixture at room temperature for 2 hr, doxorubicin hydrochloride $C_{27}H_{29}NO_{11}$, 10 mg, 0.017 mM) was added and the resulting bright red solution allowed to stir at room temperature overnight.

The solvent was removed at reduced pressure (about $10^{-4}$ torr) while the flask stood in a warm water bath. The residue left in the flask was the doxorubicin-peptide conjugate.

Example 2

Dose Response Effect of Dox-P on Drug-Resistant CHO Cell Viability

Doxorubicin and multidrug-resistant CHO cells were cultured using standard tissue culture conditions: 37° C., DMEM media, serum free conditions, with 5% $CO_2$ for pH adjustment. The cells were treated for 24 hours with either doxorubicin or Dox-P, the peptide conjugate prepared in Example 1, at concentrations of 0.25, 0.5, 0.75, and 1.0 mM. Untreated cells were used as a negative control.

Cell viability was measured using the ALAMAR BLUE™ assay (available from Biosource International, Camarillo, Calif.). The assay quantitatively measures the proliferation of cell lines and can establish the relative cytotoxicity of chemical agents. The assay incorporates a fluorometric/colorimetric growth indicator based on detection of metabolic activity. The system incorporates an oxidation-reduction (redox) indicator that both fluoresces and changes color in response to chemical reduction of growth medium resulting from cell growth. This causes the redox indicator to change from its oxidized, non-fluorescent, blue form to its reduced, fluorescent, red form. Data can be collected using either fluorescence-based instrumentation (530–560 nm excitation wavelength and 590 nm emission wavelength) or absorbance-based instrumentation (570 nm and 600 nm).

Figure 4:
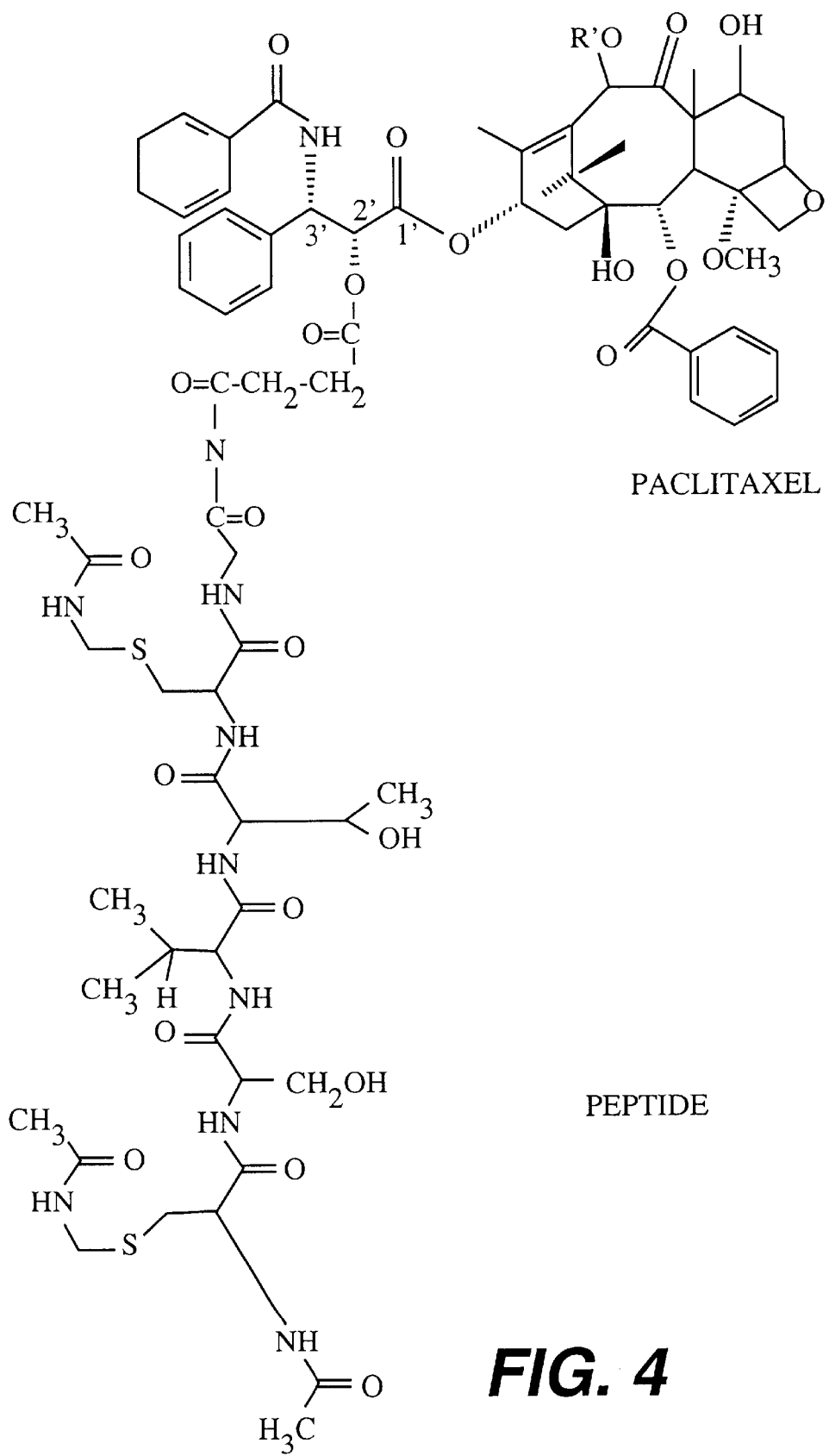
FIG. 4 (Paclitaxel-Peptide Conjugate) is a drawing of a paclitaxel-peptide conjugate (Paclitaxel-P) of the present invention, where the paclitaxel is linked through a succinyl linker to the amino terminus of the peptide Cys(Acm)-Ser-Val-Thr-Cys(Acm)-Gly (SEQ ID NO: 6). The linkage is an ester-amide linkage, with the ester linkage being between paclitaxel and the succinyl linker, and the amide linkage being between the succinyl linker and the amino terminus of the peptide.
Figure 5:
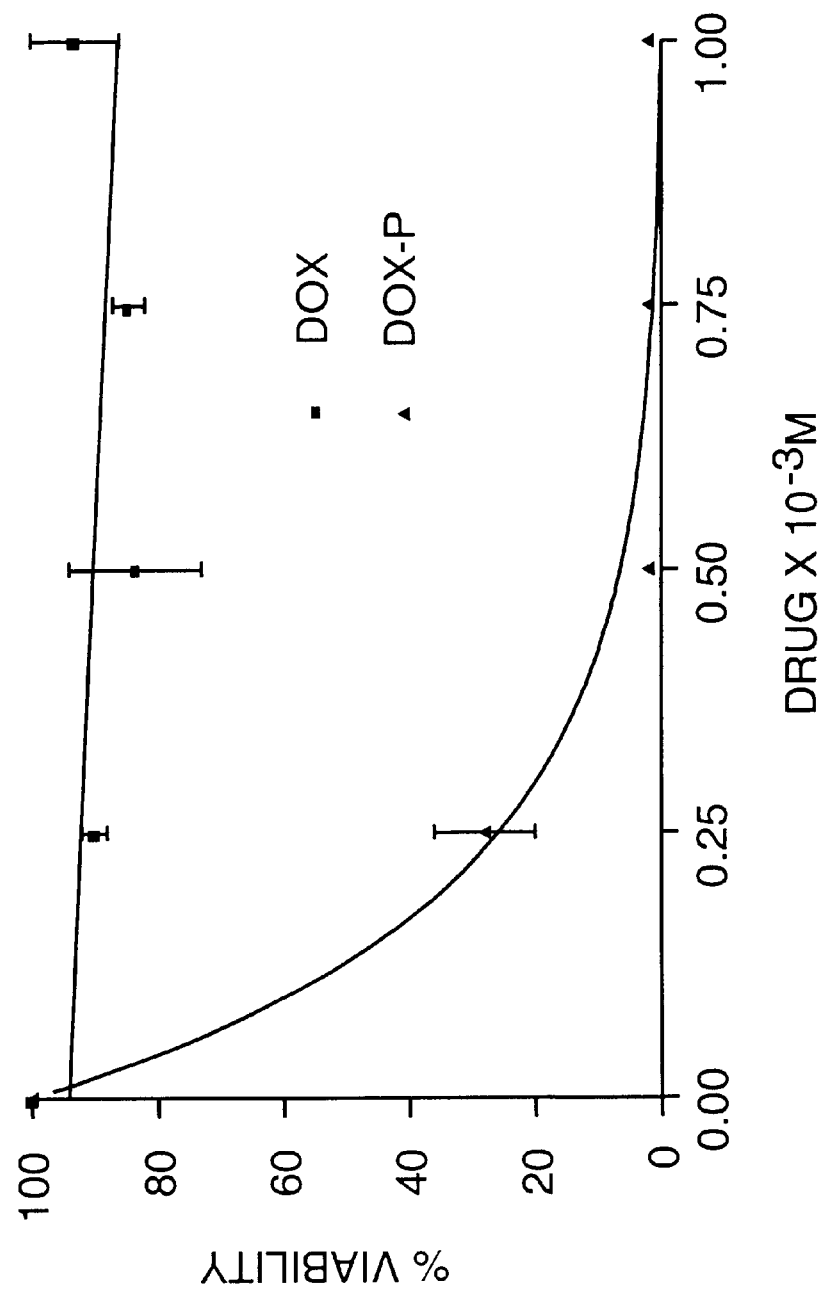
FIG. 5 (Effect of Dox and Dox-P on Drug-Resistant CHO Cell Viability) is a dose response curve showing the activity of the Dox-P on doxorubicin and multidrug-resistant CHO cells. As a control, doxorubicin alone ("Dox") is applied to the cells.

FIG. 4 shows the dramatic dose-response effect of the Dox-P conjugate compared with the negligible effect of Dox alone on the resistant CHO cells. This figure demonstrates that the Dox-P conjugate provides an effective treatment against doxorubicin and multidrug-resistant tumor cells.

Example 3

Effect of DOX and DOX-P on wild-type CHO cell viability

Figure 6:
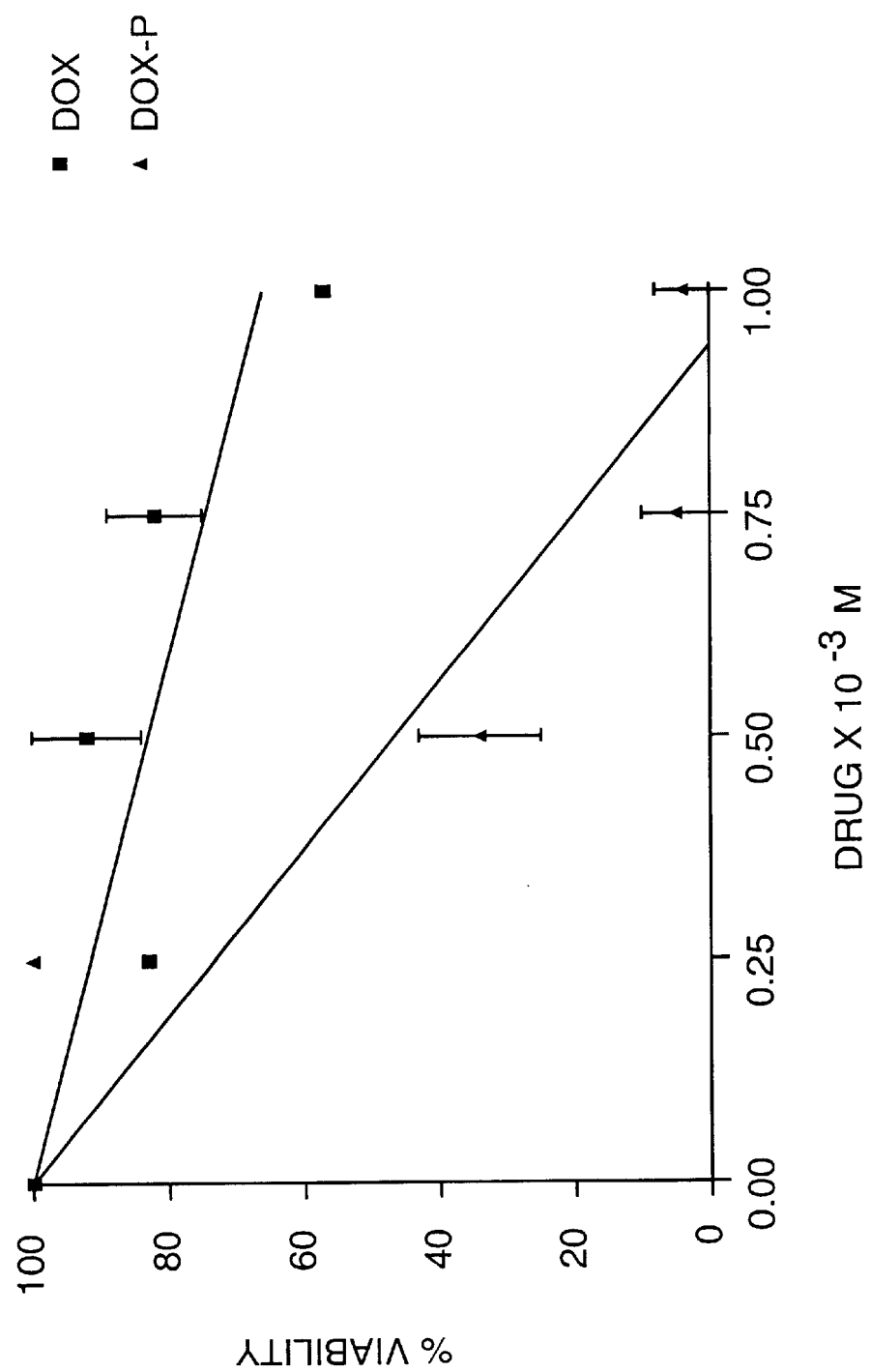
FIG. 6 (Effect of Dox and Dox-P on CHO Cell Viability) demonstrates that Dox-P appears to function more effectively against wild-type CHO cells than Dox alone.

The study of Example 2 was performed, except wild-type CHO cells were used instead of drug resistant CHO cells. This example, with results illustrated in FIG. 6, shows that the effectiveness of doxorubicin on wild-type, nonresistant cells is not hindered by the conjugation with the peptide. In fact, the data demonstrate that Dox-P appears to function more effectively against wild-type CHO cells than Dox alone.

Example 4

In Vitro $LD_{50}$ (mM) of Dox and Dox-P Conjugate

The $LD_{50}$, the dose at which half of the cells die, was calculated from Dox and Dox-P dose response curves for five different cell lines, as shown in Table 1.

TABLE 1

In Vitro $LD_{50}$ (mM) of Dox and Dox-P

| Cell Line | Dox | Dox-P |
| --- | --- | --- |
| B16-F10 Melanoma | 0.30 | 0.50 |
| Lewis Lung Carcinoma | 0.20 | 0.50 |
| Human Breast Carcinoma | 1.0 | 0.30 |
| Wild-type CHO Cells | 1.0 | 0.50 |
| Doxorubicin and multidrug-resistant CHO Cells | n/a | 0.12 |

The data for the first four cell lines demonstrates that doxorubicin's effectiveness is not significantly altered by its conjugation to the peptide, and again the doxorubicin and multidrug-resistant CHO cell line shows that the Dox-P can overcome resistance.

Example 5

Effect of Doxorubicin Peptide Conjugate on Adhesion of B16-F-10 Melanoma Cells

An adhesion study was performed to evaluate the adhesion of B16-F10 melanoma cells (a nonresistant cell line) to doxorubicin and the doxorubicin-peptide conjugate of Example 1. In a 96 well plate, duplicate wells were covered with 40 µg/ml either TSP, Dox-P, the Cys(Acm)-Ser-Val-Thr-Cys(Acm)-Gly (SEQ ID NO: 6) peptide, Dox, the scrambled peptide Val-Cys-Thr-Gly-Ser-Cys (SEQ ID NO: 3), the Cys(Acm)Ser-Val-Thr-Cys-(Acm)-Gly (SEQ ID NO: 6) peptide with a d orientation, or 1% bovine serum albumin (BSA). The wells were dried out overnight and then blocked with BSA. 100 µl of a suspension containing $2\times10^5$ B16-F-10 melanoma cells were plated in the protein covered wells and incubated at 37° C. for 20 minutes to 1 hour. The non-adherent cells were removed and the wells were washed with a Hepes buffer. The adherent cells were fixed with 2.5% glutaraldehyde for 10 minutes and stained with 0.2% Giemsa. The stain was washed off and the cells were counted in a field of 1 mm square. Cells adhering to BSA were considered background.

Figure 7:
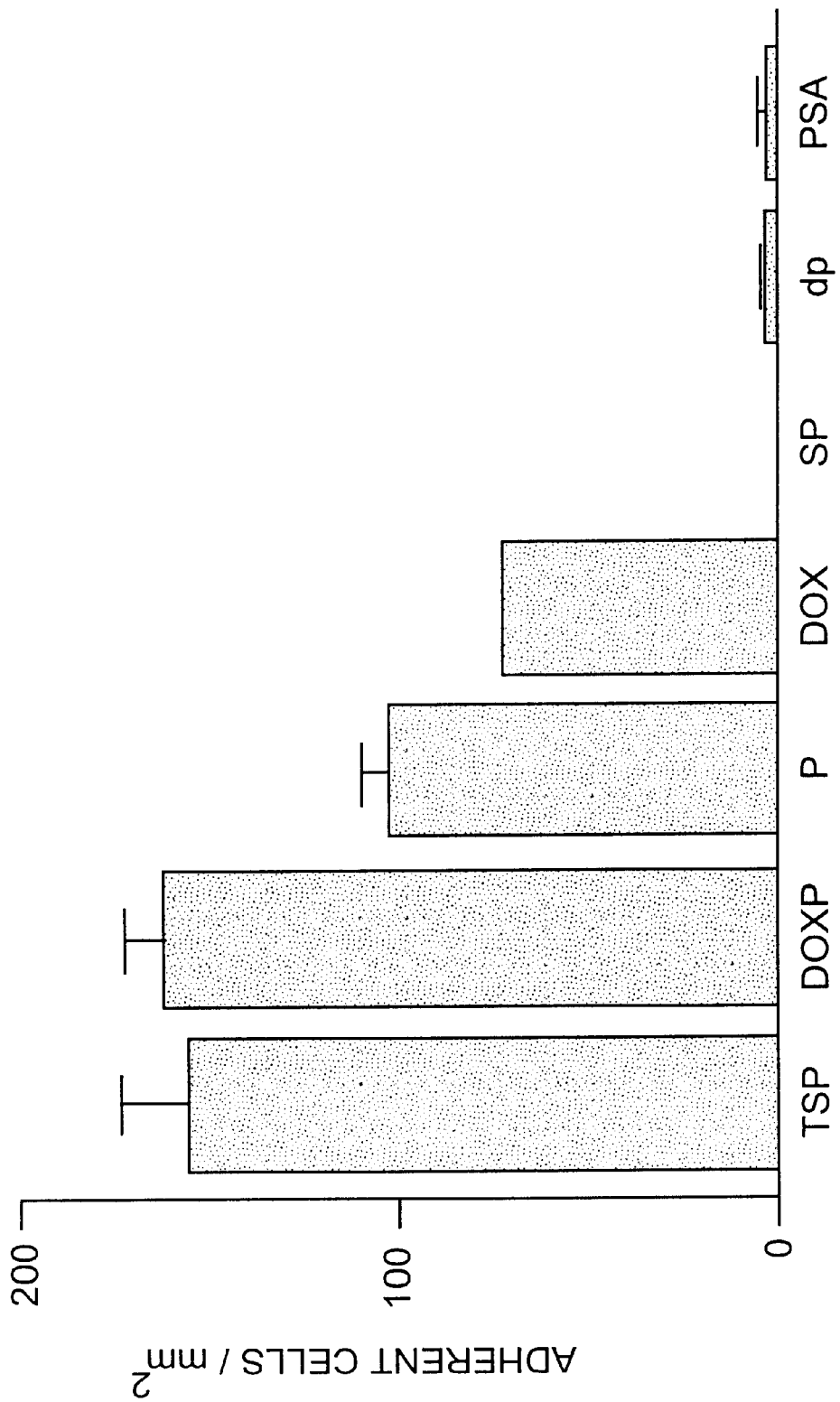
FIG. 7 (Effect of Doxorubicin Peptide Conjugate on Adhesion of B16-F10 Melanoma Cells) show the effect of Dox-P on adhesion of B16-F10 melanoma cells (a non-resistant cell line). This shows that the conjugation of the peptide with the doxorubicin does not destroy its adhesive activity.

The data are displayed in FIG. 7. This experiment shows that the peptide conjugation does not destroy, and in fact may potentiate, the adhesive activity of doxorubicin. While not wishing to be bound by any theory, it may be that the peptide's affinity to the thrombospondin receptor increases the adhesive effect of doxorubicin to the cell.

Example 6

Effect of Dox and Dox-P on Melanoma Tumor Development

Figure 8:
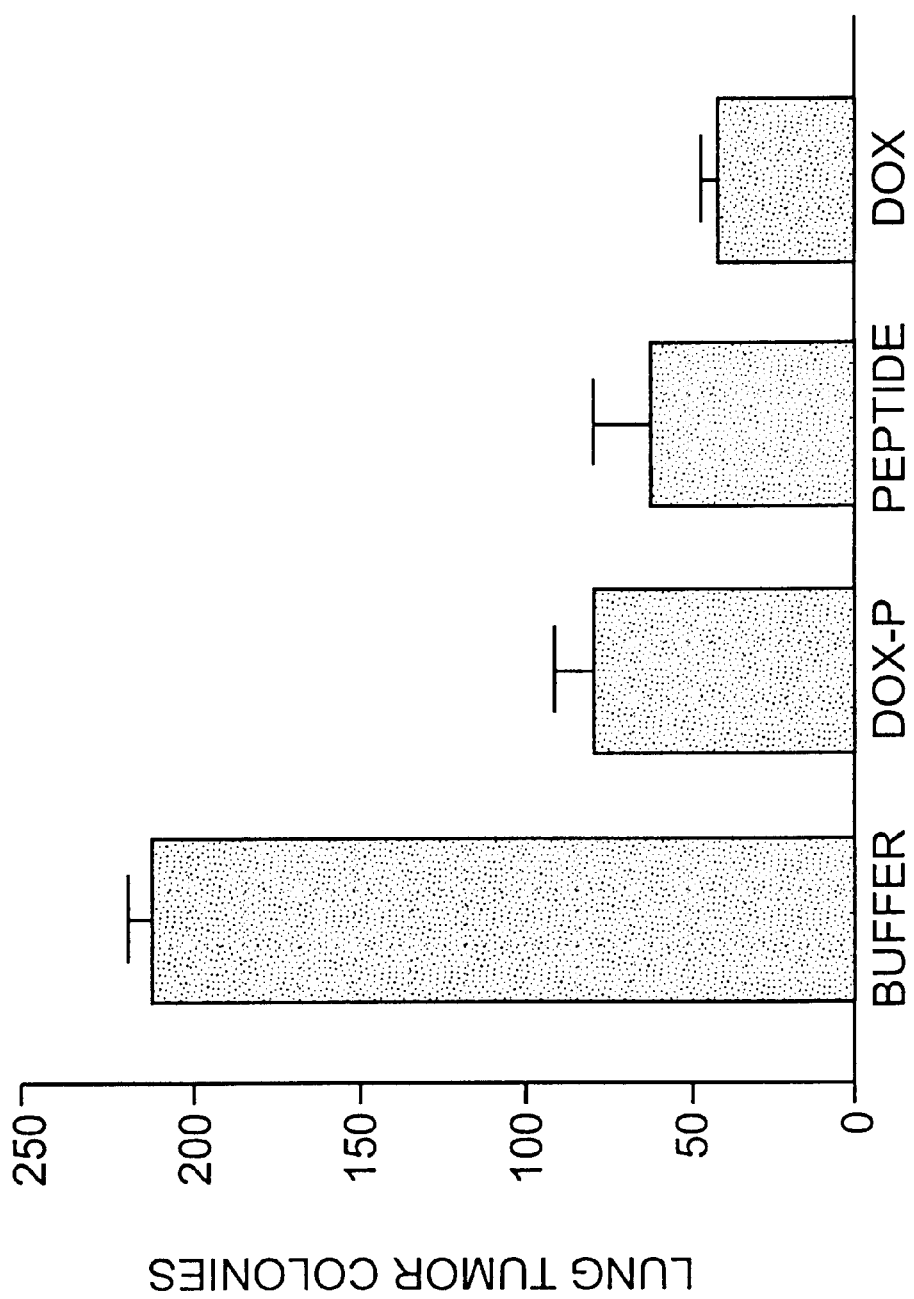
FIG. 8 (Effect of Doxorubicin (Dox), Doxorubicin-Peptide (Dox-P) on Melanoma Tumor Development) shows that Dox, Dox-P, and peptide alone all inhibit the development of lung metastasis of injected melanoma cells.

This experiment was designed to evaluate whether the conjugation of the peptide to doxorubicin altered its ability to prevent wild-type, nonresistant tumor development in mice. Melanoma tumor cells were injected into mice. The animals (5 in each group) were treated intraperitoneally 24 and 96 hours after tumor implantation with either buffer alone, Dox-P, the Cys(Acm)-Ser-Val-Thr-Cys(Acm)-Gly (SEQ ID NO: 6) peptide, or Dox, at a concentration of 18 µM/kg. The mice were sacrificed and the melanoma tumor colonies on the lung were counted. The resulting data are displayed in FIG. 8. Additionally, the tumor colonies in the Dox-P and the Dox groups were 2–5 fold smaller than in the buffer group. This demonstrates that both Dox and Dox-P were effective at preventing tumor development of this cancer that metastasizes to the lungs. Administration of the peptide alone, interestingly, also resulting in a lower number of tumors than buffer alone; however, the tumors in the peptide group had a similar size to the buffer group. These results indicate that the peptides binding to the receptor also effect tumor development, perhaps by inhibiting metalloprotease activity.

Example 7

Toxicity of Dox versus Dox-P

A toxicity study was performed using mice to evaluate the comparative toxicity levels of Dox and the Dox-P conjugate. The two compounds were administered to mice at a concentration of 30 and 68 mg/kg, respectively. Both compound have the same number of doxorubicin molecules per weight of the animal, due to the extra mass of the peptide. The toxicity of the compounds were evaluated and the data are presented in Table 2. These surprising data shows that the conjugation of the peptide to doxorubicin appears to lessen its toxicity and increase its lethal dose.

TABLE 2

Toxicity Comparison

| Composition | Mice Treated | Toxicity Results |
|---|---|---|
| Dox (30 mg/kg) | 3 | 3 mice died[1] significant weight loss |
| Dox-P (68 mg/kg) | 3 | 3 mice lived some small weight gain |
| Buffer Control | 3 | 3 mice lived some small weight gain |

[1]One mouse died from the treatment and the remaining two were so significantly ill that standard animal treatment protocols required their euthanization.

Example 8

Effect of Ala-Ser-Val-Thr-Ala-Arg (SEQ ID NO: 2) on Doxorubicin Toxicity

Doxorubicin and multidrug-resistant CHO cells were treated with a 7 coadministration of peptides and doxorubicin. In this example the peptides were not linked to the doxorubicin, but were only administered at the same time. The data are shown in FIG. 9. The Cys(Acm)-Ser-Val-Thr-Cys(Acm)-Gly (SEQ ID NO: 6) peptide did not show any effect when coadministered with the doxorubicin. Surprisingly, however, the Ala-Ser-Val-Thr-Ala-Arg (SEQ ID NO: 2) peptide shows a dose-response effect when administered with doxorubicin, overcoming the resistance mechanisms.

While not wishing to be bound by theory, it may be that the Ala-Ser-Val-Thr-Ala-Arg (SEQ ID NO: 2) peptide may cause this effect by binding to the MDR pump, inactivating it or decreasing its effectiveness. It may also bind to an additional receptor which mediates drug interaction with the cell. The Ala-Ser-Val-Thr-Ala-Arg (SEQ ID NO: 2) peptide may also interact with the membrane of the cell such that it modifies the membrane or MDR pump so as to increase permeability of the doxorubicin into the cell or decrease the cells ability to pump it out.

Example 9

Evaluation of Random Peptides by the Affinity Sensor System

A peptide's ability to bind to the thrombospondin receptor can be evaluated by the following cuvette study. One can evaluate binding of peptides to the thrombospondin receptor using the Affinity Sensor System, Cambridge, UK. This is an optical binding method that uses a cuvette to which either peptide or receptor is covalently coupled. A laser beam is used to detect bound proteins to the protein-derivatized cuvette surface. This method is highly sensitive and measures both the association and dissociation rate constants for ligand receptor interactions. The instrument assumes that one molecule of receptor binds one molecule of peptide and calculates the dissociation constant ($K_D$) according to the following relationships:

1) $k_{ass}[R][peptide] = kd_{diss}[R\text{-peptide}]$ at equilibrium, where $k_{ass}$ is the second order rate constant for association and $k_{diss}$ is the first order rate constant for dissociation
2) $K_D = [R][peptide]/[R\text{-peptide}] = k_{diss}/k_{ass}$
3) $[R\text{-peptide}]_t = [R\text{-peptide}]_{eq}[1-\exp(-k_{on}t)]$, where the instrument response measure in arc seconds is proportional to receptor-peptide complex R-peptide].
4) $k_{on} = k_{ass}[L] + k_{diss}$, where $k_{on}$ is the pseudo-first order rate constant for receptor-peptide interaction.

Thus, one can couple about 2 μg of receptor through its amino groups to COOH groups on the cuvette surface. Unreacted groups on the cuvette surface can be then blocked with ethanolamine and albumin. Peptides to be evaluated can then be applied to the cuvette at concentrations above 189 nM in HEPES buffered saline, pH 7.00, which should show saturable binding after 7 min. The dissociation constant of can then be calculated from a plot of the pseudo first order rate constant for association versus the concentration of the receptor. Thrombospondin can be used as a positive control.

Example 10

Transient Transfection and Cell Adhesion Assay

Bovine Aorta Endothelial Cells (BAEC) and MDA-MB-231 cells, breast carcinoma cells, are transfected with purified DNA encoding for the receptor by the Wizard Plus Kit (Promega, Wis.). The DNA is incorporated into the cells using the Superfect transfection reagent (Qiagen, Calif.). Cells are plated in 6 well plates and upon 80% confluency transfection is performed. 12 μl of the reagent is used as well as 2.5 μg of the DNA, with minimal concentration of 0.1 μg/μl. Superfect-DNA complex formation is performed in a serum free and antibiotic free medium. Cells are incubated at 37° C. for 3–4 hours. Then media is changed and 48 hours post transfection they are harvested for the adhesion assays.

For the adhesion assay, in a 96 well plate, duplicate wells are covered with either a peptide to be evaluated (40 μg/ml), thrombospondin "TSP-1" (40 μg/ml), fibronectin (40 μg/ml), or and 1% bovine serum albumin (BSA). The wells are dried out overnight and then blocked with BSA. 100 μl of a suspension containing $2 \times 10^5$ cells are plated in the protein covered wells and incubated at 37° C. for 20 minutes to 1 hour. The non-adherent cells are removed and the wells are washed with a Hepes buffer. The adherent cells are fixed with 2.5% glutaraldehyde for 10 minutes and stained with 0.2% Giemsa. The stain is washed off and the cells are counted in a field of 1 mm square. Cells adhering to BSA are considered background while cells adhering to TSP-1 and fibronectin are the positive control. The data can be used to evaluate which random peptides bind to the thrombospondin receptor.

Example 11

Preparation of a Paclitaxel-Peptide Conjugate

A paclitaxel-peptide conjugate ("Paclitaxel-P") was produced by the following method. TAXOL™ (paclitaxel) from the Pacific Yew Tree was purchased from ICN Biomedical Research Products, a division of ICN Pharmaceticals, Inc. and Aldrich Chemical Company (Costa Mesa, Calif.). The hexapeptide (Acm)Cys-Ser-Val-Thr-(Acm)Cys-Gly (SEQ ID NO: 6) was custom synthesized by Peptidogenics Research & Co., Inc. Acm is an acetamidomethyl protecting group for the SH of cysteine.

2'-Succinyltaxol was prepared from paclitaxel by a method similar to that described in the literature. Magri, N. F., *J. Nat. Products* 51:298 (1988); Safavy, A., *J. Med. Chem.* 42:4919 (1999). A mixture of paclitaxel (0.0168 g, 0.0196 mmol) and succinic anhydride (0.0324 g, 0.032 mmol) in pyridine (2 mL) was stirred at ambient temperature for 3.5 hours. The solvent was removed at reduced pressure and the residue stirred with water (2 mL). The resulting white solid was collected by filtration, washed with water and recrystallized from 1:1 water/acetone to give 13.9 mg of product. This was used to prepare the activated ester.

The activated ester (N-hydroxysuccinimide ester of 2' succinyltaxol) was prepared by a method similar to that used in Anderson, G. W., *J. Am. Chem. Soc.* 86:1839 (1964). A mixture of 2' succinyltaxol (0.0105 g, 0.011 mmol), N-hydroxysuccinimide (0.0029 g, 0.025 mmol) and 1-ethyl-3(3-dimethylaminopropyl)carbodiimide (0.0031 g, 0.0161 mmol) in N,N'-dimethylformamide (0.4 ml) was stirred at ambient temperature overnight. The solvent was removed at reduced pressure. Examination of the residue by thin layer chromatography ($SiO_2$, 10% methanol/90% chloroform) revealed the absence of the more polar 2'-succinyltaxol and the presence of a less polar N-hydroxysuccinimide ester. The white solid residue containing the activated ester was used without further purification in the conjugation step.

To the activated ester in N,N'-dimethylformamide (0.4 mL), was added a solution of the hexapeptide (Acm)Cys-Ser-Val-Thr-(Acm)Cys-Gly (0.0076 g, 0.0106 mmol) and $NaHCO_3$ (0.0020 g, 0.0238 mmol) in N,N'-dimethylformamide (0.4 mL) and water (0.4 mL). The mixture was stirred at ambient temperature overnight and the solvent removed at reduced pressure. The resulting residue was subjected to preparative thin layer chromatography (1000 micron $SiO_2$, 1:1 EtOAc/$CH_3OH$). Several bands were observed including starting material. A polar band was extracted from the silica gel using the elution solvent to develop the plate. Removal of the solvent gave a very viscous, clear, thick gel material. Comparative thin layer chromatography revealed that it was not starting material.

Example 12

Evaluation of the Paclitaxel-P Conjugate

The effectiveness of the paclitaxel-p conjugate can be tested through a variety of means. A cytotoxicity assay can be used to evaluate the effectiveness of the conjugate versus paclitaxel alone. For example, normal cancer cells (such as human breast cancer cells) and paclitaxel-resistant cells can be cultured using standard tissue culture conditions: 37° C., DMEM medium, serum free conditions, with 5% $CO_2$ for pH adjustment. The cells may then be treated for 24 hours with either paclitaxel alone or the paclitaxel-p conjugate prepared in Example 11, at concentrations of 0.25, 0.5, 0.75, and 1.0 mM. Untreated cells can be used as a negative control.

Cell viability can then be measured using the ALAMAR BLUE™ assay (available from Biosource International, Camarillo, Calif.). The assay quantitatively measures the proliferation of cell lines and can establish the relative cytotoxicity of chemical agents. The assay incorporates a fluorometric/colorimetric growth indicator based on detection of metabolic activity. The system incorporates an oxidation-reduction (redox) indicator that both fluoresces and changes color in response to chemical reduction of growth medium from cell growth. This causes the redox indicator to change from its oxidized, non-fluorescent, blue form to its reduced, fluorescent, red form. Data can be collected using either fluorescence-based instrumentation (530–560 nm excitation wavelength and 590 nm emission wavelength) or absorbance-based instrumentation (570 nm and 600 nm).

Example 13

In Vitro $LD_{50}$ (mM) of Paclitaxel and Paclitaxel-P Conjugate

The $LD_{50}$, the dose at which half of the cells die, can be calculated from paclitaxel and paclitaxel-p dose response curves for various cell line, including B16-F10 melanoma, lewis lung carcinoma, human breast carcinoma, wild type CHO cells, and paclitaxel resistant cells, and multidrug resistant cells. An example of a paclitaxel resistant cell line is the SKOV-3TR ovarian cancer cell line. Feller et al., *Discovery of differentially expressed genes associated with paclitaxel resistance using cDNA array technology, Clin. Caner Res.* 5(11):3445–53 (1999).

Example 14

Effect of Paclitaxel-Peptide Conjugate on Adhesion of B16-F10 Melanoma Cells

An adhesion study can be performed to evaluate the adhesion of B16-F10 melanoma cells (a nonresistant cell line) to paclitaxel and the paclitaxel-peptide conjugate of Example 11. This study could also be performed with a breast cancer cell line. In a 96 well plate, duplicate wells are covered with 40 µg/ml either TSP, paclitaxel-p, the Cys (Acm)-Ser-Val-Thr-Cys(Acm)-Gly (SEQ ID NO: 6) peptide, paclitaxel, the scrambled peptide Val-Cys-Thr-Gly-Ser-Cys (SEQ ID NO: 3), the Cys(Acm)-Ser-Val-Thr-Cys (Acm)-Gly (SEQ ID NO: 6) peptide with a d orientation, or 1% bovine serum albumin (BSA). The wells are dried out overnight and then blocked with BSA. 100 µl of a suspension containing $2 \times 10^5$ B16-F-10 melanoma cells is plated in the protein covered wells and incubated at 37° C. for 20 minutes to 1 hour. The non-adherent cells are removed and the wells are washed with a Hepes buffer. The adherent cells are fixed with 2.5% glutaraldehyde for 10 minutes and stained with 0.2% Giemsa. The stain is washed off and the cells are counted in a field of 1 mm square. Cells adhering to BSA were considered background.

Example 15

Effect of Paclitaxel and Paclitaxel-P on Melanoma Tumor Development

This experiment can evaluate whether the conjugation of the peptide to doxorubicin alters its ability to prevent wild-type, nonresistant tumor development in mice. Melanoma tumor cells are injected into mice. The animals (5 in each group) are treated intraperitoneally 24 and 96 hours after tumor implantation with either buffer alone, paclitaxel-p, the Cys(Acm)-Ser-Val-Thr-Cys(Acm)-Gly (SEQ ID NO: 6) peptide, or paclitaxel, at a concentration of which is lower than the $LD_{50}$, preferably 10 fold lower than the $LD_{50}$. The mice are sacrificed and the melanoma tumor colonies on the lung are counted. The $LD_{50}$ can be determined experimentally by treating groups of mice with increasing doses of paclitaxel and identifying the concentration at which half of the animals die after an acute treatment regimen.

Example 16

Toxicity of Paclitaxel Versus Paclitaxel-P

A toxicity study can be performed using mice to evaluate the comparative toxicity levels of paclitaxel and the paclitaxel-P conjugate. The paclitaxel is administered to mice at a concentration which is lower than the $LD_{50}$, which can be determined as in Example 15, preferably 10 fold lower than the $LD_{50}$. The paclitaxel-p conjugage is administered at a dose that yields the same number of paclitaxel molecules per weight of the animal, due to the extra mass of the peptide. The toxicity of the compounds are then evaluated.

Example 17

Effect of Ala-Ser-Val-Thr-Ala-Arg (SEQ ID NO: 2) on Paclitaxel Toxicity

Paclitaxel and multidrug-resistant CHO cells are treated with a coadministration of peptides and paclitaxel. In this example the peptides are not linked to the paclitaxel, but are only administered at the same time. It is expected that the Cys(Acm)-Ser-Val-Thr-Cys(Acm)-Gly (SEQ ID NO: 6) peptide will not show any effect when coadministered with the paclitaxel.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All documents cited herein are incorporated by reference.

We claim:

1. A method of treating a patient suffering from cancer, wherein a cancer chemotherapy agent is selected, conjugated to a peptide, and at least one dose is administered to the patient in a therapeutically effective amount, and wherein the peptide binds to a receptor for thrombospondin.

2. The method of claim 1, wherein the method is used to treat a patient with drug resistant cancer.

3. The method of claim 1, wherein the method is used to treat a patient with cancer, wherein the cancer is not a drug resistant cancer.

4. The method of claim 1, wherein the chemotherapy agent is selected from the group consisting of doxorubicin and paclitaxel.

5. The method of claim 1, wherein the peptide targets the chemotherapy agent to the cancer to be treated.

6. The method of claim 1, wherein the peptide binds to a receptor for thrombospondin.

7. A method of treating a patient suffering from cancer, wherein a cancer chemotherapy agent is selected, a peptide is selected, and at least one dose of the agent and peptide are coadministered to the patient in a therapeutically effective amount, wherein the peptide binds to a receptor for thrombospondin.

8. The method of claim 7, wherein the chemotherapy agent is selected from the group consisting of doxorubicin and paclitaxel.

9. The method of claim 7, wherein the peptide targets the chemotherapy agent to the cancer to be treated.

10. The composition of claim 7, wherein the peptide is Ala-Ser-Val-Thr-Ala-Arg (SEQ ID NO: 2).

11. A composition for treating a patient suffering from cancer, wherein the composition comprises a chemotherapy agent and a peptide, wherein the peptide is not Arg-Gly-Asp or Asn-Gly-Asp.

12. The composition of claim 11, wherein the composition is used to treat a patient with drug resistant cancer.

13. The composition of claim 11, wherein the chemotherapy agent is conjugated to the peptide.

14. The composition of claim 13, wherein the peptide is Cys(Acm)-Ser-Val-Thr- Cys(Acm)-Gly (SEQ ID NO: 6).

15. The composition of claim 13, wherein the peptide is Ala-Ser-Val-Thr-Ala-Arg (SEQ ID NO: 2).

* * * * *

UNITED STATES PATENT AND TRADEMARK OFFICE
CERTIFICATE OF CORRECTION

PATENT NO.    : 6,377,954 B1
DATED         : April 23, 2002
INVENTOR(S)   : Yoshifusa Togawa It is certified that error appears in the above-identified patent and that said Letters Patent is hereby corrected as shown below:

<u>Title page,</u>
Item [56], References Cited, U.S. PATENT DOCUMENTS, sixth listed reference, change "Bresleau et al." to -- Breslau et al. --.

<u>Column 8,</u>
Line 37, change "an" to -- a --.

Signed and Sealed this

Third Day of September, 2002

Attest:

Attesting Officer

JAMES E. ROGAN
*Director of the United States Patent and Trademark Office*